(12) United States Patent
Del Río Pericacho et al.

(10) Patent No.: US 10,421,719 B2
(45) Date of Patent: Sep. 24, 2019

(54) MALEIC ACID SALT OF A SILODOSIN INTERMEDIATE

(71) Applicant: URQUIMA, S.A., Sant Fost de Capsentelles, Barcelona (ES)

(72) Inventors: José Luis Del Río Pericacho, Barcelona (ES); Xavier Vila Tusell, Barcelona (ES)

(73) Assignee: URQUIMA S.A., Barcelona (ES)

( * ) Notice: Subject to any disclaimer, the term of this patent is extended or adjusted under 35 U.S.C. 154(b) by 0 days.

(21) Appl. No.: 15/763,689

(22) PCT Filed: Sep. 29, 2016

(86) PCT No.: PCT/ES2016/070682
§ 371 (c)(1),
(2) Date: Mar. 27, 2018

(87) PCT Pub. No.: WO2017/055664
PCT Pub. Date: Apr. 6, 2017

(65) Prior Publication Data
US 2018/0265469 A1  Sep. 20, 2018

(30) Foreign Application Priority Data
Sep. 30, 2015 (ES) ................................. 201531398

(51) Int. Cl.
*C07D 209/42* (2006.01)
*A61K 31/404* (2006.01)

(52) U.S. Cl.
CPC .......... *C07D 209/42* (2013.01); *A61K 31/404* (2013.01)

(58) Field of Classification Search
CPC .................................................. C07D 209/42
See application file for complete search history.

(56) References Cited

U.S. PATENT DOCUMENTS

| | | | |
|---|---|---|---|
| 5,387,603 A | 2/1995 | Kitazawa et al. | |
| 6,310,086 B1 | 10/2001 | Kitazawa et al. | |
| 7,834,193 B2 | 11/2010 | Yamaguchi et al. | |
| 8,013,007 B2 | 9/2011 | Liu | |
| 8,471,039 B2 | 6/2013 | Joshi et al. | |
| 9,163,243 B2 | 10/2015 | Schulzhen et al. | |
| 9,394,251 B2 | 7/2016 | Zhang et al. | |
| 9,745,264 B2 | 8/2017 | Gu et al. | |
| 9,862,681 B2 | 1/2018 | Singh et al. | |
| 9,932,308 B2 | 4/2018 | Motoyama et al. | |
| 9,938,239 B2 | 4/2018 | Kumar Luthra et al. | |
| 2014/0243544 A1 | 8/2014 | Wang et al. | |
| 2016/0304452 A1 | 10/2016 | Gu et al. | |
| 2017/0008950 A1 | 1/2017 | Capon | |

FOREIGN PATENT DOCUMENTS

| | | |
|---|---|---|
| CN | 101302183 B | 11/2008 |
| CN | 101412690 A | 4/2009 |
| CN | 101759627 A | 6/2010 |
| CN | 101993406 A | 3/2011 |
| CN | 101993407 A | 3/2011 |
| CN | 101585798 B | 6/2011 |
| CN | 102115455 A | 7/2011 |
| CN | 102311319 A | 1/2012 |
| CN | 102320996 A | 1/2012 |
| CN | 102382029 A | 3/2012 |
| CN | 102690223 A | 9/2012 |
| CN | 102746210 A | 10/2012 |
| CN | 103420893 B | 12/2013 |
| CN | 101993405 B | 1/2014 |
| CN | 103554003 B | 2/2014 |
| CN | 103848772 A | 6/2014 |
| CN | 104140389 A | 11/2014 |
| CN | 104230782 A | 12/2014 |
| CN | 102702067 B | 1/2015 |
| CN | 104557662 B | 4/2015 |
| CN | 104744336 B | 7/2015 |
| CN | 103265470 B | 10/2015 |
| CN | 104974072 B | 10/2015 |
| CN | 102382029 B | 6/2016 |
| CN | 106045892 A | 10/2016 |
| CN | 106045895 A | 10/2016 |
| CN | 106083689 A | 11/2016 |
| CN | 106380438 A | 2/2017 |
| CN | 106496092 A | 3/2017 |
| CN | 106995399 A | 8/2017 |
| EP | 0600675 A1 | 6/1994 |
| EP | 1541554 A1 | 6/2005 |
| EP | 1806340 A1 | 7/2007 |
| IN | 1380/MUM/2011 | 12/2012 |
| IN | 2119/MUM/2010 | 2/2014 |
| IN | 3274/CHE/2013 | 1/2015 |
| IN | 483/MUM/2014 | 11/2015 |
| IN | 724/CHE/2014 | 12/2015 |
| IN | 6154/CHE/2015 | 1/2016 |
| IN | 1394/DEL/2014 | 8/2016 |

(Continued)

OTHER PUBLICATIONS

International Search Report, dated Jan. 3, 2017.

*Primary Examiner* — Shawquia Jackson
(74) *Attorney, Agent, or Firm* — Tristan A. Fuierer; Olive Law Group, PLLC

(57) ABSTRACT

The present invention relates to a salt of formula (I), the preparation method for preparing same, and the use thereof in the preparation of silodosin.

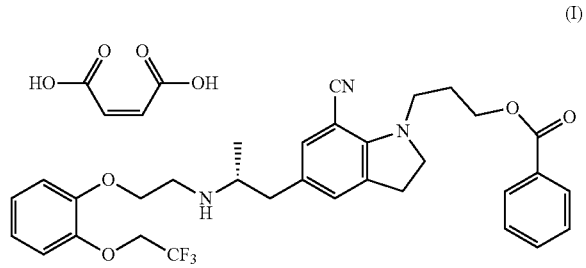

(I)

18 Claims, 3 Drawing Sheets

(56) References Cited

FOREIGN PATENT DOCUMENTS

| | | |
|---|---|---|
| IN | 5186/CHE/2014 | 8/2016 |
| JP | 3331048 B2 | 12/1995 |
| JP | 4634560 B2 | 2/2011 |
| JP | 4921646 B2 | 4/2012 |
| JP | 2015151395 A | 8/2015 |
| JP | 6242298 B2 | 1/2016 |
| JP | 2016064988 A | 4/2016 |
| JP | 2006188470 A | 5/2016 |
| JP | 2016088847 A | 5/2016 |
| JP | 6068569 B2 | 1/2017 |
| KR | 20150066777 A | 6/2015 |
| KR | 20150066782 A | 6/2015 |
| KR | 20150098478 A | 8/2015 |
| KR | 20160027536 A | 3/2016 |
| KR | 20160027537 A | 3/2016 |
| KR | 1628946 B1 | 6/2016 |
| KR | 20160074769 A | 6/2016 |
| KR | 20160109736 A | 9/2016 |
| KR | 101686087 B1 | 12/2016 |
| WO | 9943652 A1 | 9/1999 |
| WO | 2006046499 A1 | 5/2006 |
| WO | 2008106125 A2 | 9/2008 |
| WO | 2011030356 A2 | 3/2011 |
| WO | 2011101864 A1 | 8/2011 |
| WO | 2011124704 A1 | 10/2011 |
| WO | 2012014186 A1 | 2/2012 |
| WO | 2012062229 A1 | 5/2012 |
| WO | 2012131710 A2 | 10/2012 |
| WO | 2012147019 A1 | 11/2012 |
| WO | 2012147107 A2 | 11/2012 |
| WO | 2013056842 A1 | 4/2013 |
| WO | 2013056852 A1 | 4/2013 |
| WO | 2013072935 A2 | 5/2013 |
| WO | 2013097456 A1 | 7/2013 |
| WO | 2014060571 A1 | 4/2014 |
| WO | 2014118606 A2 | 8/2014 |
| WO | 2014134005 A2 | 9/2014 |
| WO | 2014167507 A1 | 10/2014 |
| WO | 2015015512 A2 | 2/2015 |
| WO | 2015080457 A1 | 6/2015 |
| WO | 2015085827 A1 | 6/2015 |
| WO | 2015119057 A1 | 8/2015 |
| WO | 2015126076 A1 | 8/2015 |
| WO | 2015138907 | 9/2015 |
| WO | 2015154637 A1 | 10/2015 |
| WO | 2016042441 A1 | 3/2016 |
| WO | 2016139773 | 9/2016 |
| WO | 2016189552 A2 | 12/2016 |
| WO | 2017051324 A1 | 3/2017 |
| WO | 2017080414 A1 | 5/2017 |

MALEIC ACID SALT OF A SILODOSIN INTERMEDIATE

CROSS-REFERENCE TO RELATED APPLICATIONS

This application is filed under the provisions of 35 U.S.C. § 371 and claims the priority of International Patent Application No. PCT/ES2016/070682 filed on 29 Sep. 2016 entitled "MALEIC ACID SALT OF A SILODOSIN INTERMEDIATE" in the name of José Luis DEL RÍO PERICACHO, et al., which claims priority to Spanish Patent Application No. P201531398, filed on 30 Feb. 2016, both of which are hereby incorporated by reference herein in their entirety.

FIELD OF THE INVENTION

The present invention relates to a maleic acid salt of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate of formula (I)

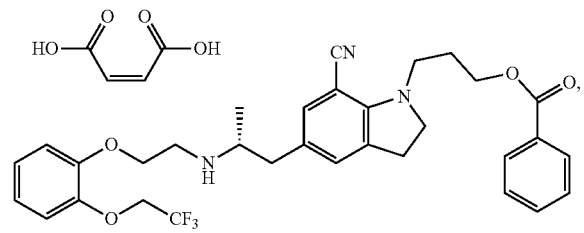

(I)

which is a key precursor in silodosin production, a preparation method for preparing said salt, and the use thereof in the preparation of silodosin.

BACKGROUND OF THE INVENTION

Silodosin, the chemical structure of which is represented by means of formula (V) below

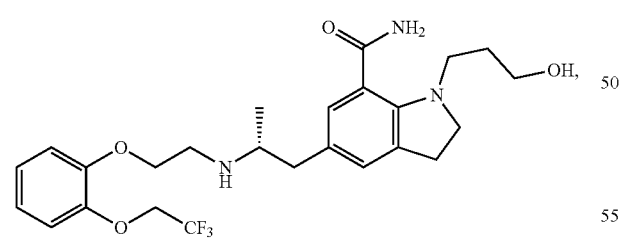

(V)

is an α-adrenergic receptor antagonist selective for $\alpha_{1A}$ adrenergic receptors that are mainly located in the prostate, the base and neck of the bladder, and the prostatic capsule and urethra. Blocking these receptors causes smooth muscle relaxation which reduces bladder outlet resistance without affecting detrusor smooth muscle contractility, improving storage (irritative) symptoms and emptying (obstructive) symptoms associated with benign prostate hyperplasia. Silodosin has a substantially lower affinity for $\alpha_{1B}$ adrenergic receptors located in the cardiovascular system. Due to these characteristics, silodosin is used in the treatment of signs and symptoms of benign prostate hyperplasia.

Silodosin, the preparation method thereof, and the therapeutic use thereof are described in patent document EP 0 600 675 A1. The methods described in this patent document involve the alkylation of primary amine derivatives either with a halogenated derivative or with an activated alcohol in order to yield a secondary amine intermediate and to then convert same into silodosin. To purify the intermediate and end products in the preparation of silodosin, patent document EP 0 600 675 A1 describes the use of column chromatography, which entails a drawback for carrying out the method on an industrial level.

Silodosin production methods which avoid using steps of purification by means of column chromatography have been described. In this sense, patent document EP 1 806 340 A1 describes the formation of an oxalate salt of the compound of formula (II) (an intermediate in silodosin synthesis)

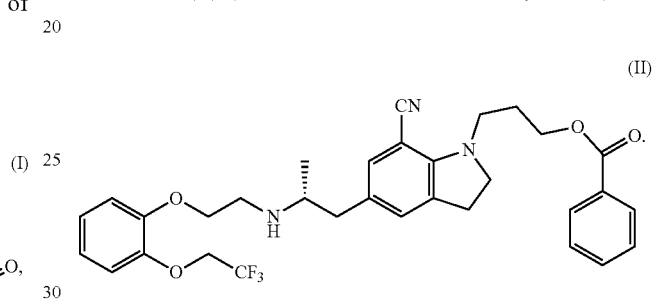

(II)

Patent document EP 1 806 340 A1 describes the production of the compound of formula (II) by means of an alkylation reaction of the amine of formula (III)

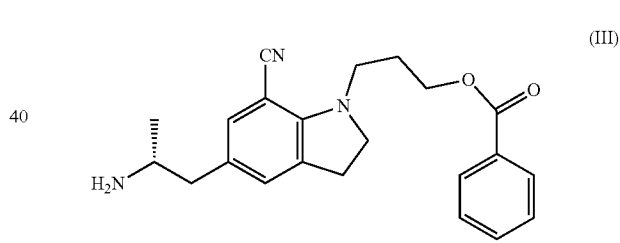

(III)

with a compound of formula (IV)

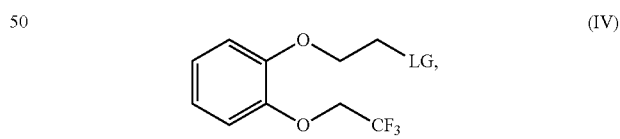

(IV)

wherein LG is a leaving group; and subsequent conversion of the compound of formula (II) that has been obtained into silodosin. The method described in patent document EP 1 806 340 A1 comprises the formation of the oxalate salt of the compound of formula (II), which is a solid that can be isolated by crystallization, and can therefore be separated from the impurities that remain dissolved in the reaction medium.

Patent document WO 2012/147019 A1 describes a similar method comprising the formation of the tartrate salt of the compound of formula (II), also in solid form.

There is a need to provide alternative methods for silodosin synthesis which allow obtaining said product on an industrial scale, facilitating the steps of purification and manipulation of the method.

SUMMARY OF THE INVENTION

The inventors have investigated alternative methods for silodosin synthesis which allow obtaining said product on an industrial scale, facilitating the steps of purification and manipulation of the method, particularly alternative methods of purifying the compound of formula (II) (key intermediate in silodosin production). In this sense, the inventors have tried to purify the compound of formula (II) by means of the formation of maleate, glycolate, citrate, succinate, fumarate, hydrochloride, hydrobromide, sulfate, phosphate, acetate, or methanesulfonate salts of the amine of formula (II). Surprisingly, as shown in Example 1 herein, of all the tested acids, maleic acid is the only one that yields a salt of the compound of formula (II) in solid form, and it can therefore be separated by filtration and is suitable for the separation of impurities, particularly those impurities that remain dissolved in the reaction medium in this step of formation of said intermediate (II), and is therefore advantageous for silodosin production on an industrial scale. Furthermore, the formation of a solid intermediate has advantages in terms of manipulating the intermediate in silodosin production.

Therefore, in a first aspect, the present invention relates to the maleic acid salt of formula (I)

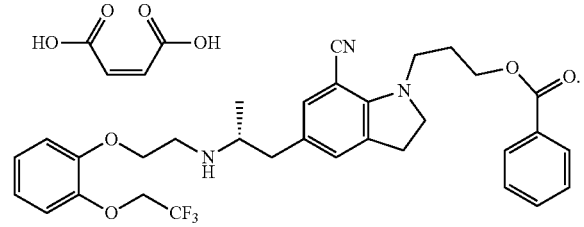

(I)

In a second aspect, the invention relates to a method for preparing the maleic acid salt of formula (I)

(I)

which comprises:
a) treating the compound of formula (II)

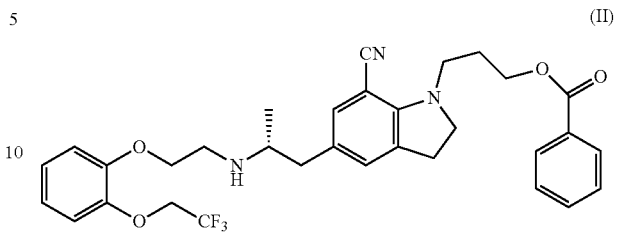

(II)

with maleic acid; and
b) isolating the salt of formula (I).

In a third aspect, the invention relates to a preparation method for preparing silodosin of formula (V)

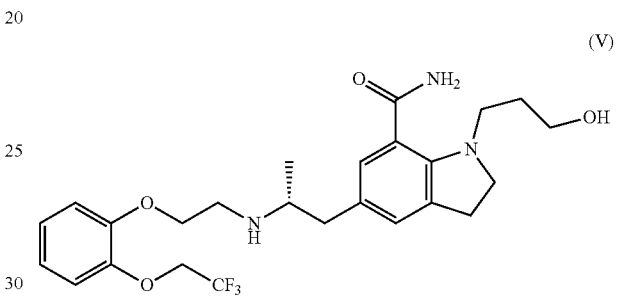

(V)

which comprises hydrolyzing the salt of formula (I) for the silodosin of formula (V).

DETAILED DESCRIPTION OF THE INVENTION

Salt of Formula (I)

Figure 1:
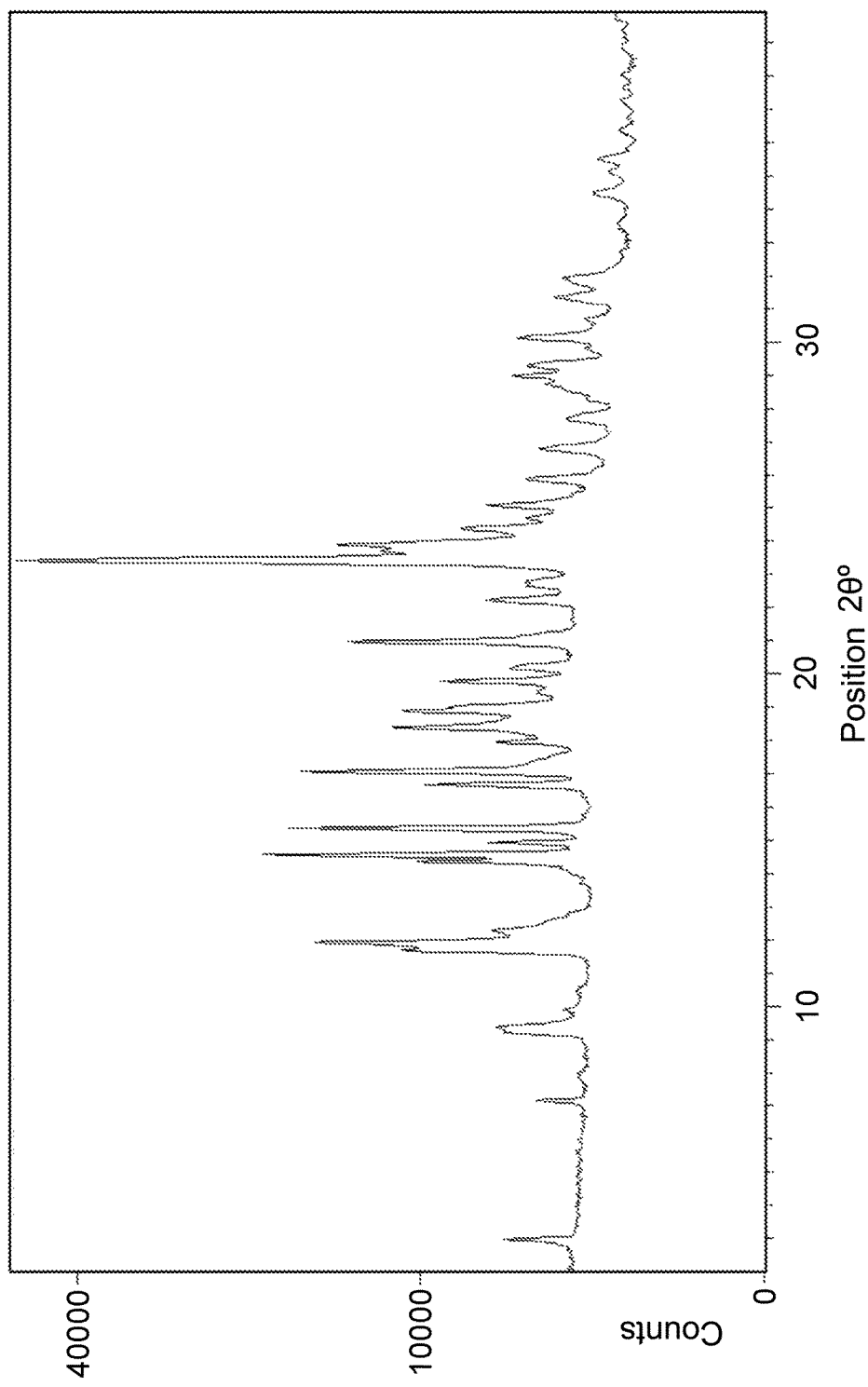
FIG. 1 shows the X-ray powder diffractogram of the polymorph of the salt of formula (I) obtained in Example 2.

In a first aspect, the invention relates to the maleic acid salt of formula (I)

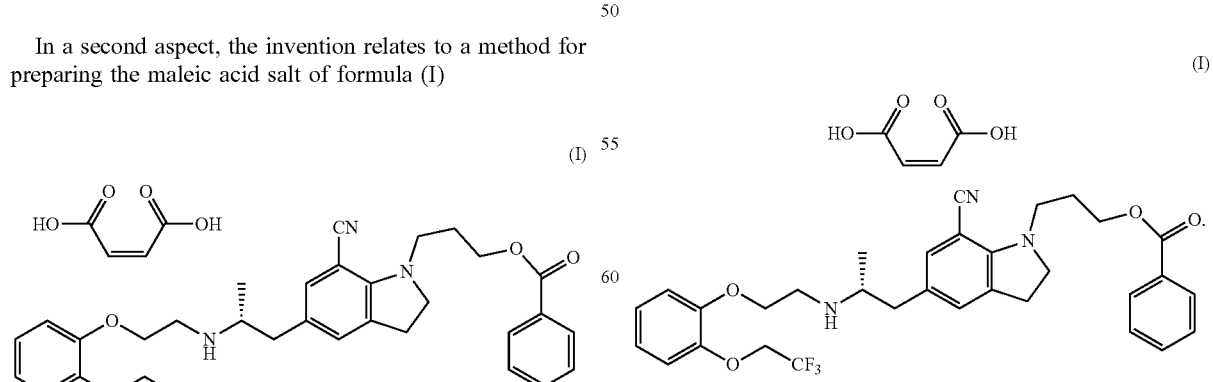

(I)

In said salt of formula (I), the maleic acid and 3-{7-cyano-5-[(2R)-2-({2-[2-(2,2,2-trifluoroethoxy)phenoxy]ethyl}amino)propyl]-2,3-dihydro-1H-indol-1-yl}propyl benzoate are at a molar ratio of about 1:1, i.e., there is one mol of maleic acid for every mol of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate present in the salt.

Said salt can also be in solvate form, particularly hydrate or alcoholate, such as isopropanolate, for example.

The term "solvate" according to this invention must be understood to mean any form of the salt of formula (I) having another molecule (generally a polar solvent) bound thereto through a non-covalent bond. The solvates include, in particular, hydrates and alcoholates, for example isopropanolate.

In a preferred embodiment, the present invention relates to a polymorph of the compound of formula (I), characterized in that the X-ray powder diffractogram thereof (recorded with a copper X-ray source) has peaks at 11.9, 14.6, 15.4, 17.1, 18.4, 21.0, 23.4, and 23.9 2θ°±0.2 2θ°.

The expression "±0.2 2θ°" refers to the measurement error and means that the value indicated for each of the peaks may be comprised in the range defined by the indicated value−0.2 2θ° and the indicated value+0.2 2θ°.

In a preferred embodiment, the polymorph of the compound of formula (I) is characterized in that its X-ray powder diffractogram (recorded with a copper X-ray source) furthermore has peaks at 11.7, 14.4, 16.7, and 18.9 2θ°±0.2 2θ°. More preferably, the X-ray powder diffractogram (recorded with a copper X-ray source) of said polymorph furthermore has peaks at 19.0, 19.8, 22.2, 24.4, and 25.1 2θ°±0.2 2θ°. More preferably, the X-ray powder diffractogram (recorded with a copper X-ray source) of said polymorph furthermore has peaks at 3.0, 9.2, 9.4, 12.3, 14.9, 17.9, 20.2, 24.7, 25.9, 29.0, 29.3, and 30.1 2θ°±0.2 2θ°. In a particular embodiment, the polymorph is characterized by the X-ray powder diffractogram (recorded with a copper X-ray source) having the peaks, and preferably also the relative intensities, shown in Table 1.

TABLE 1

X-ray powder diffractogram of the compound of formula (I)

| Position (2θ°) | Relative intensity (%) |
|---|---|
| 3.0 | 6.1 |
| 7.2 | 3.61 |
| 9.2 | 6.81 |
| 9.4 | 7.52 |
| 9.9 | 1.5 |
| 11.7 | 17.82 |
| 11.9 | 31.48 |
| 12.3 | 8.08 |
| 14.4 | 16.73 |
| 14.6 | 40.83 |
| 14.9 | 8.79 |
| 15.4 | 37.41 |
| 16.7 | 16.05 |
| 17.1 | 34.63 |
| 17.9 | 8.26 |
| 18.4 | 20.63 |
| 18.9 | 19.06 |
| 19.0 | 12.14 |
| 19.4 | 4.81 |
| 19.8 | 14.53 |
| 20.2 | 6.96 |
| 21.0 | 27.11 |
| 22.2 | 9.63 |
| 22.7 | 5.9 |
| 22.8 | 5.87 |
| 23.4 | 100 |
| 23.9 | 29.07 |
| 24.4 | 12.61 |

TABLE 1-continued

X-ray powder diffractogram of the compound of formula (I)

| Position (2θ°) | Relative intensity (%) |
|---|---|
| 24.7 | 6.05 |
| 25.1 | 9.86 |
| 25.9 | 6.37 |
| 26.8 | 5.22 |
| 27.6 | 2.97 |
| 28.3 | 1.87 |
| 28.7 | 4.79 |
| 29.0 | 7.72 |
| 29.3 | 6.45 |
| 30.1 | 7.12 |
| 30.7 | 2.22 |
| 31.4 | 4.37 |
| 31.9 | 3.77 |

In a particular embodiment, said polymorph of the compound of formula (I) has an X-ray powder diffractogram (recorded with a copper X-ray source) substantially like the one shown in FIG. 1.

Said polymorph can be obtained by means of isopropanol recrystallization of the compound of formula (I).

In the present document, the terms "compound of formula (I)", "salt of formula (I)", "maleic acid salt of formula (I)" are used interchangeably and refer to the maleic acid salt of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate.

Preparation Method for Preparing the Salt of Formula (I)

In a second aspect, the invention relates to a method for preparing the maleic acid salt of formula (I) defined above, which comprises:

a) treating the compound of formula (II)

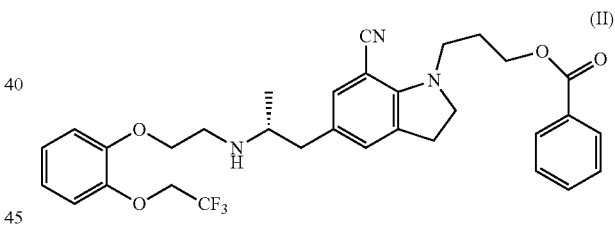

with maleic acid; and b) isolating the maleic acid salt of formula (I).

Step a) is preferably performed in a solvent selected from the group consisting of methanol, ethanol, n-propanol, isopropanol, tert-butanol, n-butanol, and mixtures thereof, preferably isopropanol.

Said solvent may optionally furthermore contain other minor components present at no more than 20% v/v, preferably no more than 15% v/v, more preferably no more than 10% v/v, more preferably no more than 5% v/v, even more preferably no more than 1% v/v. Said minor components can be, among others, water and polar aprotic solvents.

The term "polar aprotic solvent" refers to a polar solvent that has no hydrogen atoms bound to an electronegative atom and capable of forming hydrogen bridges such as, for example, hydrogen atoms of the OH and NH groups and the dielectric constant of which is at least 3, said dielectric constant being the ratio between the capacitance of a solvent-filled capacitor and the capacitance of the capacitor at 20-25° C. The values of the dielectric constant of several solvents are described, for example, in "Vogel's Textbook of Practical Organic Chemistry", 5$^{th}$ edition, Appendix. Examples of polar aprotic solvents are acetonitrile, tetrahydrofuran, ethyl acetate, butyl acetate, acetone, methylisobutylketone, ethylmethylketone, dimethylformamide, dimethylsulfoxide, dichloromethane, nitromethane, and propylene carbonate, among others.

Particularly, the polar aprotic solvent present as a minor component in the solvent used in step a) is the polar aprotic solvent used in the preparation of the compound of formula (II), preferably acetonitrile.

The volume of solvent suitable for step a) can be readily determined by one skilled in the art and it will depend on the particular solvent used. Preferably, between 20 L and 60 L of solvent are used per kg of maleic acid, more preferably between 30 L and 50 L of solvent per kg of maleic acid, even more preferably between 35 L and 45 L per kg of maleic acid, most preferably about 40 L per kg of maleic acid.

The treatment of step a) is preferably performed stirring the mixture of compound of formula (II), maleic acid, and solvent to dissolution, more preferably at a temperature between 40° C. and 60° C., even more preferably between 45° C. and 55° C., most preferably about 50° C.

Once said mixture has dissolved, it is preferably cooled at a temperature not higher than 25° C., more preferably between 15° C. and 25° C., more preferably between 20° C. and 25° C., even more preferably about 20° C., maintaining stirring, preferably between 10 h and 50 h, more preferably between 10 h and 40 h, more preferably between 10 h and 30 h, more preferably between 10 h and 20 h, more preferably at least 15 h.

In a particular embodiment, the maleic acid and the compound of formula (II) of step a) are at a molar ratio of between 1.5:1 and 1:1, preferably between 1.2:1 and 1:1, more preferably between 1.1:1 and 1:1, more preferably of about 1.1:1.

In the context of the present invention, the ends of the mentioned ranges must be considered as part of said ranges unless otherwise indicated.

Synthesis of the compound of formula (II) has been described previously, for example, in patent documents EP 1806340 A1 and WO 2021/147019 A1, which are incorporated herein by reference.

In a particular embodiment, the compound of formula (II) of step a) is obtained by means of treating the compound of formula (III) or a salt thereof

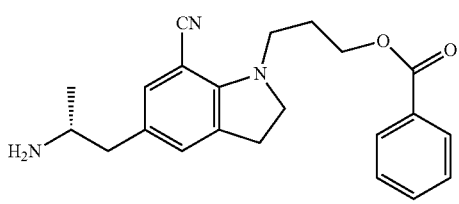

(III)

with a compound of formula (IV)

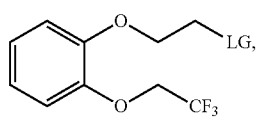

(IV)

wherein LG is a leaving group,
in a polar aprotic solvent, and in the presence of a base, to yield the compound of formula (II).

The term "leaving group" refers to the fragment of the molecule which is shifted by the amino group of the compound of formula (III) to form compound (II). Leaving groups are known to one skilled in the art. Examples of suitable leaving groups for the compound of formula (IV) are $C_1$-$C_6$ alkylsulfonyloxy, such as methanesulfonyloxy ($CH_3$—$SO_3$—); $C_1$-$C_6$ haloalkylsulfonyloxy, such as trifluoromethanesulfonyloxy ($CF_3$—$SO_3$—); arylsulfonyloxy, such as benzenesulfonyloxy (Ph-$SO_3$—), toluenesulfonyloxy ((p-$CH_3$)-Ph-$SO_3$—), p-bromobenzenesulfonyloxy ((p-Br)-Ph-$SO_3$—), o-nitrobenzenesulfonyloxy ((o-$NO_2$)-Ph-$SO_3$—), and p-nitrobenzenesulfonyloxy ((p-$NO_2$)-Ph-$SO_3$—); halogen atom, such as chlorine (Cl—), bromine (Br—), and iodine (I—). The leaving group is preferably selected from the group consisting of $C_1$-$C_3$ alkylsulfonyloxy, $C_1$-$C_3$ haloalkylsulfonyloxy, arylsulfonyloxy, and a halogen atom. More preferably, the leaving group is selected from the group consisting of methanesulfonyloxy, trifluoromethanesulfonyloxy, toluenesulfonyloxy, chlorine, bromine, and iodine. Even more preferably, the leaving group is selected from the group consisting of methanesulfonyloxy, trifluoromethanesulfonyloxy, and toluenesulfonyloxy. In the most preferred embodiment, the leaving group is methanesulfonyloxy.

The term "alkyl" refers to a radical with a linear or branched hydrocarbon chain which consists of carbon and hydrogen atoms, does not contain unsaturations, has the number of carbon atoms indicated in each case (for example $C_1$-$C_6$ means having 1 to 6 carbon atoms), and is bound to the rest of the molecule by means of a single bond. Examples of alkyl are methyl, ethyl, n-propyl, isopropyl, isobutyl, n-butyl, tert-butyl, pentyl, hexyl, etc.

The term "aryl" refers to an aromatic hydrocarbon radical which consists of carbon and hydrogen atoms, contains between 6 and 18 carbon atoms, and is bound to the rest of the molecule by means of a single bond, such as phenyl, naphthyl, or anthracyl, preferably phenyl. The aryl radical can be optionally substituted with one or more substituents (such as one, two, or three substituents) independently selected from the group consisting of $C_1$-$C_6$ alkyl (preferably $C_1$-$C_3$ alkyl), halogen, and nitro ($NO_2$).

The term "halogen" or "halo" refers to an atom selected from F, Cl, Br, and I.

The term "alkylsulfonyloxy" refers to an alkyl group as defined above which is bound to a sulfonyloxy (—$SO_3$—) group, and wherein said sulfonyloxy group is bound to the rest of the molecule by means of a single bond. An example of alkylsulfonyloxy is methanesulfonyloxy.

The term "haloalkylsulfonyloxy" refers to an alkylsulfonyloxy group as defined above, which further comprises one or more (such as one, two, three, four, five, or six) halogen atoms as substituents of the alkyl group. An example of haloalkylsulfonyloxy is trifluoromethanesulfonyloxy.

The term "arylsulfonyloxy" refers to an aryl group as defined above which is bound to a sulfonyloxy (—$SO_3$—) group, and wherein said sulfonyloxy group is bound to the rest of the molecule by means of a single bond. Examples of arylsulfonyloxy are benzenesulfonyloxy, toluenesulfonyloxy, p-bromobenzenesulfonyloxy, o-nitrobenzenesulfonyloxy, and p-nitrobenzenesulfonyloxy.

In a particular embodiment, the polar aprotic solvent used in obtaining the compound of formula (II) of step a) by means of treating the compound of formula (III) or a salt thereof with a compound of formula (IV) is selected from the group consisting of acetonitrile, tetrahydrofuran, ethyl acetate, butyl acetate, acetone, methylisobutylketone, ethylmethylketone, dimethylformamide, dimethylsulfoxide, dichloromethane, nitromethane and propylene carbonate, and a mixture thereof. The organic solvent used is preferably acetonitrile.

In a preferred embodiment, the tartaric acid salt of the compound of formula (III), preferably the (2R,3R)-(+)-tartaric acid salt, is used in obtaining the compound of formula (II) of step a) by means of treating the compound of formula (III) or a salt thereof with a compound of formula (IV), as described above.

A base is used in obtaining the compound of formula (II) of step a) by means of treating the compound of formula (III) or a salt thereof with a compound of formula (IV). Said base can be an inorganic base, such as an alkali metal hydroxide (for example, sodium hydroxide or potassium hydroxide), an alkali metal carbonate (for example, sodium carbonate, potassium carbonate, cesium carbonate), or it can also be an organic base, such as a $C_1$-$C_6$ di- or tri-alkylamine (for example, triethylamine, diethylamine, and diisopropylamine), for example. In a particular embodiment, the base is an inorganic base, more preferably an alkali metal carbonate, even more preferably potassium carbonate. Preferably, the base and the compound of formula (III) or a salt thereof are at a molar ratio of between 3:1 and 1:1, preferably between 2.5:1 and 1:1, more preferably 2:1 and 1:1.

In obtaining the compound of formula (II) of step a) by means of treating the compound of formula (III) or a salt thereof with a compound of formula (IV), said treatment is preferably performed with stirring at reflux temperature of the solvent. Preferably, said treatment is performed by means of stirring between 10 h and 50 h, more preferably between 10 h and 40 h, more preferably between 10 h and 30 h, more preferably about 24 h.

In obtaining the compound of formula (II) of step a) by means of treating the compound of formula (III) or a salt thereof with a compound of formula (IV), the compound of formula (IV) and the compound of formula (III) or the salt thereof are at a molar ratio of between 1.5:1, preferably between 1.2:1.

Once step a) of treating the compound of formula (II)

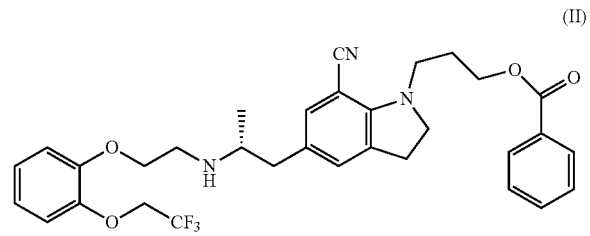 [SMILES: C[C@H](Cc1cc(C#N)c2c(c1)CCN2CCCOC(=O)c1ccccc1)NCCOc1ccccc1OCC(F)(F)F]

(II)

with maleic acid has been performed, the next step of the method for obtaining the salt of formula (I) is to isolate said salt (step b)), i.e., separate the salt of formula (I) from the reaction medium.

The isolation of the salt of formula (I) can be performed by means of conventional methods known in the art, such as centrifugation, filtration, or a combination of both, for example.

Optionally, the salt of formula (I) can be purified (step c)) using conventional techniques, such as by means of washes with a solvent (particularly one or more washes, such as one, two, or three washes, preferably with the solvent used in step a), by means of recrystallization, or by means of a combination of both techniques, for example. In a particular embodiment, the salt of formula (I) is purified by means of one or more washes with the solvent used in step a).

Preparation Method for Preparing Silodosin

In another aspect, the present invention relates to a preparation method for preparing silodosin of formula (V)

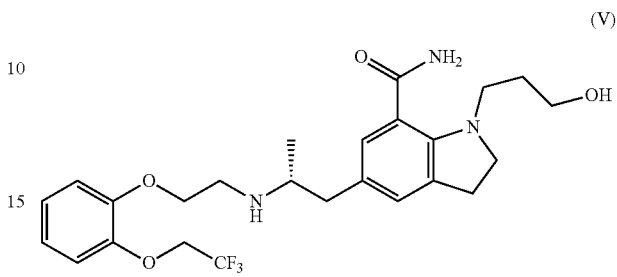

(V)

which comprises hydrolyzing the salt of formula (I) to yield silodosin of formula (V).

In a preferred embodiment, the salt of formula (I) is obtained by means of a method as defined above.

Obtaining silodosin from said salt of formula (I) comprises hydrolyzing benzoic acid ester to yield the corresponding alcohol group and hydrolyzing the nitrile group to yield the corresponding amido group, and to therefore give silodosin. Said hydrolyses can be carried out simultaneously, or the ester group can be hydrolyzed first followed by the nitrile group. Said ester and nitrile hydrolyses can be performed in one and the same reactor (known as a one-pot reaction) or step-by-step in different reactors; they are preferably performed in one and the same reactor.

Hydrolysis of the ester group can be performed by means of standard ester hydrolysis reaction conditions to yield the corresponding alcohol which are known to one skilled in the art and are described, for example, in March's Advanced Organic Chemistry: Reactions, Mechanisms and Structure [Michael B. Smith and Jerry March, 6th edition, Wiley-Interscience, John Wile & Sons, Inc. Hoboken, N.J., 2007]. In a particular embodiment, said hydrolysis is carried out by means of treatment with a base, such as an alkali metal hydroxide, for example, sodium hydroxide or potassium hydroxide; an alkali metal carbonate, for example, sodium carbonate, potassium carbonate, or cesium carbonate. Preferably, the base used is an alkali metal hydroxide, more preferably sodium hydroxide. Said hydrolysis can also be performed by means of treatment with an acid, such as hydrochloric acid, hydrobromic acid, sulfuric acid, or nitric acid.

Hydrolysis of the nitrile group can be performed by means of standard nitrile hydrolysis reaction conditions to yield the corresponding amide which are known to one skilled in the art and are described, for example, in March's Advanced Organic Chemistry: Reactions, Mechanisms and Structure [Michael B. Smith and Jerry March, 6th edition, Wiley-Interscience, John Wile & Sons, Inc. Hoboken, N.J., 2007]. In a particular embodiment, said hydrolysis is carried out by means of treatment with a base, such as an alkali metal hydroxide, for example, sodium hydroxide or potassium hydroxide; an alkali metal carbonate, for example, sodium carbonate, potassium carbonate, or cesium carbonate. Preferably, the base used is an alkali metal hydroxide, more preferably sodium hydroxide. Said hydrolysis can also be performed by means of treatment with an acid, such as hydrochloric acid, hydrobromic acid, sulfuric acid, or nitric acid. Preferably, hydrolysis of the nitrile group is carried out in the presence of an oxidizing agent, preferably hydrogen peroxide.

Therefore, in a particular embodiment, hydrolysis of the salt of formula (I) to yield silodosin is performed in the presence of a base or an acid, as defined above, more preferably in the presence of a base, even more preferably in the presence of an alkali metal hydroxide, preferably sodium hydroxide. Said treatment allows hydrolyzing both the ester and the nitrile of the salt of formula (I) in addition to generating the free base of the salt.

In a most preferred embodiment, hydrolysis is furthermore performed in the presence of an oxidizing agent, such as hydrogen peroxide.

A solvent suitable for carrying out the hydrolysis of the salt of formula (I) is dimethylsulfoxide. Therefore, in a particular embodiment dimethylsulfoxide is used as a solvent.

Hydrolysis is preferably performed with stirring at a temperature between 20° C. and 60° C., even more preferably between 30° C. and 50° C., most preferably about 40° C., preferably between 10 min and 60 min, more preferably between 10 min and 40 min, even more preferably between 15 min and 30 min.

Silodosin can be isolated from the reaction medium by means of conventional methods known in the art, such as liquid-liquid extraction, centrifugation, filtration, or combination thereof, for example, by means of liquid-liquid extraction and filtration.

The silodosin that is obtained can be purified by means of washes, recrystallization, or a combination of both, for example by means of washes with toluene, recrystallization of toluene or isopropyl acetate, washes and recrystallization of toluene, or washes with toluene and recrystallization of isopropyl acetate. Different polymorphs of silodosin, such as, for example, beta polymorph and gamma polymorph of silodosin, which are previously described in patent document EP 1 541 554 B1, can also be obtained.

In a particular embodiment, the beta or gamma polymorphs of silodosin have a particle size $D_{90}$ of 200 µm to 800 µm.

The particle size of silodosin or of any of its polymorphs, the $D_{90}$ of which is 200 µm to 800 µm, can be reduced by means of techniques known to one skilled in the art, such as milling, micronizing, grinding, or a combination of said techniques optionally accompanied by one or more sieving operations. Particularly, the particle size can be reduced by milling and/or micronizing.

In a particular embodiment, the milled gamma polymorph of silodosin is characterized by the following particle sizes: $D_{90}$=45.5 µm and/or D[4,3]=20.1 µm.

In another particular embodiment, the micronized gamma polymorph of silodosin is characterized by the following particle sizes: $D_{90}$=12 µm and/or D[4,3]=6.8 µm.

In another particular embodiment, the milled beta polymorph of silodosin is characterized by the following particle sizes: $D_{90}$=73.7 µm, $D_{50}$=27.5 µm and/or D[4,3]=37.7 µm.

$D_x$, which can also be written as D(v, 0.X) means that X % by volume of the particles have a diameter smaller than the specified diameter D. Therefore, $D_{90}$ (or D(v, 0.9)) of 100 µm means that 90% by volume of the particles have a diameter smaller than 100 µm.

D[4,3] refers to the mean particle diameter (by volume).

Particle size can be determined by means of conventional techniques known to one skilled the art, such as laser diffraction, particularly by means of a Malvern Mastersizer 2000 particle size analyzer, using the experimental protocol described in the corresponding section of materials and methods of the examples.

The following non-limiting examples intend to illustrate the present invention and must not be interpreted as limiting the scope of the present invention.

EXAMPLES

Materials and Methods
Nuclear Magnetic Resonance (NMR):
  Bruker equipment, 300 MHz for $^1$H-NMR and 75.5 MHz for $^{13}$C-NMR. The deuterated solvent is $CDCl_3$.
Infrared (IR) Spectroscopy:
  Perkin Elmer FT-IR equipment with the ATR (direct measurement) technique.
HPLC-Mass Spectrometry (MS):
  Alliance-Waters 2695 System equipped with PDA detector and connected to ESCi+/−micromass ZQ "single quadrupole" ionization equipment.
X-ray Powder Diffraction:
  The powdered sample was placed between polyester films 3.6 microns thick. A PANalytical X'Pert PRO MPD theta/theta powder diffractometer with a radius of 540 mm or of 240 mm was used in a converging-beam configuration with a focusing mirror and a geometry of transmission with the flat samples placed between two low-absorption films. Cu Kα radiation (λ=1.5418 Å). Operating power: 45 kV-40 mA. Incident beam slits at a beam height of 0.4 mm. Soller slit of 0.02 radians of diffracted incident beam. PIXcel detector: Active length=3.347°. 2θ/θ scans of 2 to 40 2θ° with a pass of 0.026 2θ° and a measurement time of 300 seconds per pass (diffractometer with a radius of 540 mm), or alternatively 2θ/θ scans of 5 to 30 2θ° with a pass of 0.026 2θ° and a measurement time of 2000 seconds per pass (diffractometer with a radius of 240 mm).
Particle size:
Instrument conditions:
Apparatus: Malvern Mastersizer 2000
Accessory: Hydro 2000SM (A)
Recirculation: 2500 rpm
Dispersing agent: Milli-Q grade purified water
Sample preparation: About 50 mg of sample are weighed on a watch glass, 3 to 5 drops of 0.2% Nonidet P40 (nonylphenylpolyethyleneglycol) are added, and it is mixed with a spatula until forming a homogeneous paste, making sure that the particle aggregates of the product are broken up. The paste is transferred to a 50 mL beaker with the help of 10 mL of water which are added with a dropper, making sure to entrain as much sample as possible. The solution is left in an ultrasound bath for 1 minute, during which time alignment is performed and equipment background is set, recirculating water through the circuit.
Method: Without leaving the sample to stand and with the help of a dropper, the required amount of suspension to be studied, in the dispersion unit, is added to obtain an obscuration of about 15%. Reading is performed after checking that the obscuration remains constant (about 10%). Internal ultrasounds of the equipment are not applied.
Milling/Micronizing:
  An Alpine Hosokawa 100 AFG mill type M4-GMP is used in both cases. To mill/micronize silodosin, the working conditions of the Alpine Hosokawa 100 AFG mill are adjusted such that the particle size obtained is the desired one.

Comparative Example 1. Formation of salts of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate Fifty grams of 5-[(2R)-2-aminopropyl]-1-[3-(bezoyloxy)propyl]-2,3-dihydro-1H-indol-7-carbonitrile (2R,3R)-2,3-dihydroxybutanedioate (tartrate salt of the compound of formula (III), 26.9 g of $K_2CO_3$, 39.8 g of 2-[2-(2,2,2-trifluoroethoxy)phenoxy]ethyl methanosulfonate and 250 mL of acetonitrile are introduced in a 500 mL reactor with mechanical stirring. It is heated to reflux for 24 h. After this time has elapsed, it is cooled at 20° C. and AcOEt (400 mL) and water (250 mL) are added. It is stirred for 30 min, and the phases are separated. The organic phase is dried with anhydrous sodium sulfate, filtered and concentrated to dryness, obtaining 70.9 g of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate (free base). Eighteen grams of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate are weighed and dissolved in 90 mL of 96% EtOH. Fifteen milliliters are distributed in different balloons. A different acid (for example, 0.60 g of maleic acid) dissolved in 15 mL of 96% EtOH is added to each balloon. It is left under stirring at room temperature for two hours, and then cooled at 0-5° C., maintaining stirring. In the case of maleic acid, the maleate precipitates after 30 minutes. If a salt is formed, it is filtered, washed with 96° C. EtOH and vacuum dried. Table 2 shows the result obtained with different acids.

TABLE 2

| Acid | Molar ratio | Solvent | Result |
|---|---|---|---|
| Maleic | 1 | EtOH | Solid |
| Glycolic | 1 | EtOH | Solution |
| Citric monohydrate | 1 | EtOH | Solution |
| Succinic | 1 | EtOH | Solution |
| Fumaric | 1 | EtOH | Solution |
| HCl in EtOH | 2 | EtOH | Solution |
| HBr | 2 | EtOH | Solution |
| $H_2SO_4$ | 2 | EtOH | Solution |
| $H_3PO_4$ | 3 | EtOH | Solution |
| Acetic | 2 | EtOH | Solution |
| Methanesulfonic | 2 | EtOH | Solution |
| Tartaric | 1 | EtOH | Solid |
| Oxalic | 1.02 | EtOH | Solid |

The results of Table 2 show that only tartaric and oxalic acids (described in the state of the art) and maleic acid (present invention) yield the salt of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate in solid form, and are therefore suitable for separating the dialkylated impurity in the silodosin production method.

Example 2. Synthesis of the maleic acid salt of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate of formula (I)

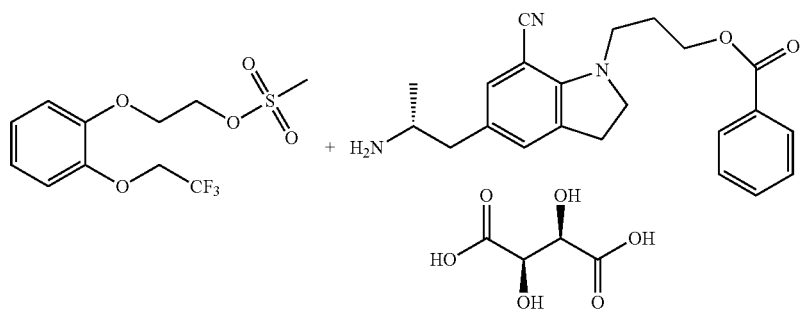

(1) ACN, $K_2CO_3$
(2) $H_2O$
(3) IPA/maleic acid

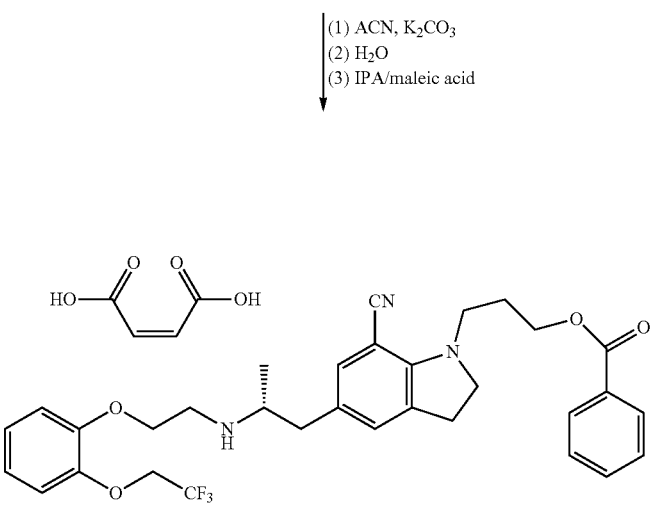

5-[(2R)-2-aminopropyl]-1-[3-(bezoyloxy)propyl]-2,3-dihydro-1H-indol-7-carbonitrile (2R,3R)-2,3-dichydroxybutanedioate (tartrate salt of the compound of formula (III); 1 kg), 2-[2-(2,2,2-trifluoroethoxy)phenoxy]ethyl methanesulfonate (0.7 kg), and potassium carbonate (0.5 kg) were loaded in a reactor. Acetonitrile (ACN, 5 L) was loaded in the reactor under nitrogen atmosphere. The content of the reactor was then mixed and heated to reflux under nitrogen atmosphere. The mixture was kept under reflux for 24 h. The reactor was then cooled at 50° C. and water (3 L) was loaded in the reactor. The content of the reactor was cooled and kept at 20° C. for 15 min. The phases were left to separate, the aqueous phase was removed, and the remaining content was distilled under reduced pressure at 70° C. Isopropanol (IPA, 5 L) and a solution of maleic acid (0.25 kg) in isopropanol (5 L) were loaded in the reactor. The reaction mixture was heated at 50° C. and kept at this temperature until complete dissolution. The content of the reactor was cooled and kept at 20° C. for at least 15 h. The suspension obtained was centrifuged, washed with isopropanol (3 L), and left to drain for 3 h. The product obtained was then vacuum dried for 2 h at room temperature and for about 5 h at 35° C. The X-ray powder diffractogram of the solid obtained is shown in FIG. 1 and the peaks are listed in Table 1 (described above).

$^1$H-NMR (CDCl$_3$, 300 MHz): δ 1.37 (d, J=6.6 Hz, 3H), 2.13 (qn, J=6.6 Hz, 2H), 2.69 (dd, J=9.0, 13.8 Hz, 1H), 2.93 (t, J=8.7 Hz, 2H), 3.10 (dd, J=5.1, 13.5 Hz, 1H), 3.40-3.60 (m, 5H), 3.73 (t, J=7.2 Hz, 2H), 4.37 (t, J=3.9 Hz, 2H), 4.38 (q, J=8.4 Hz, 2H), 4.44 (t, J=6.5 Hz, 2H), 6.22 (s, 2H), 6.80-7.00 (m, 6H), 7.43 (t, J=7.5 Hz, 2H), 7.56 (tt, J=1.6, 7.65 Hz, 1H), 8.05 (d, J=8.4 Hz, 2H) ppm.

$^{13}$C-NMR (CDCl$_3$, 75.5 MHz): δ 15.4, 27.0, 27.1, 38.5, 43.9, 45.0, 53.2, 55.6, 62.4, 65.0, 67.3, 87.7, 115.3, 116.4, 119.1, 122.6, 123.4, 123.9, 124.2, 128.3, 129.4, 129.6, 130.0, 132.0, 132.9, 133.2, 135.8, 147.4, 148.0, 152.0, 166.7, 169.8 ppm. MS (m/z): 582.8 [M+1]$^+$. IR: ν (cm$^{-1}$): 2200, 1717.

Example 3. Synthesis of the Gamma Polymorph of Silodosin

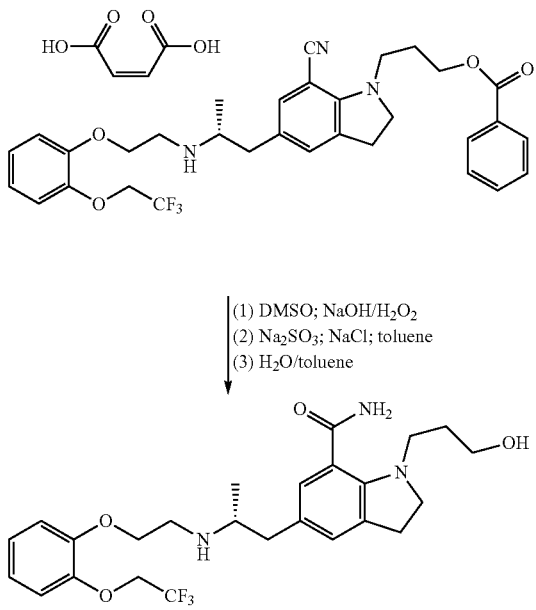

Figure 2:
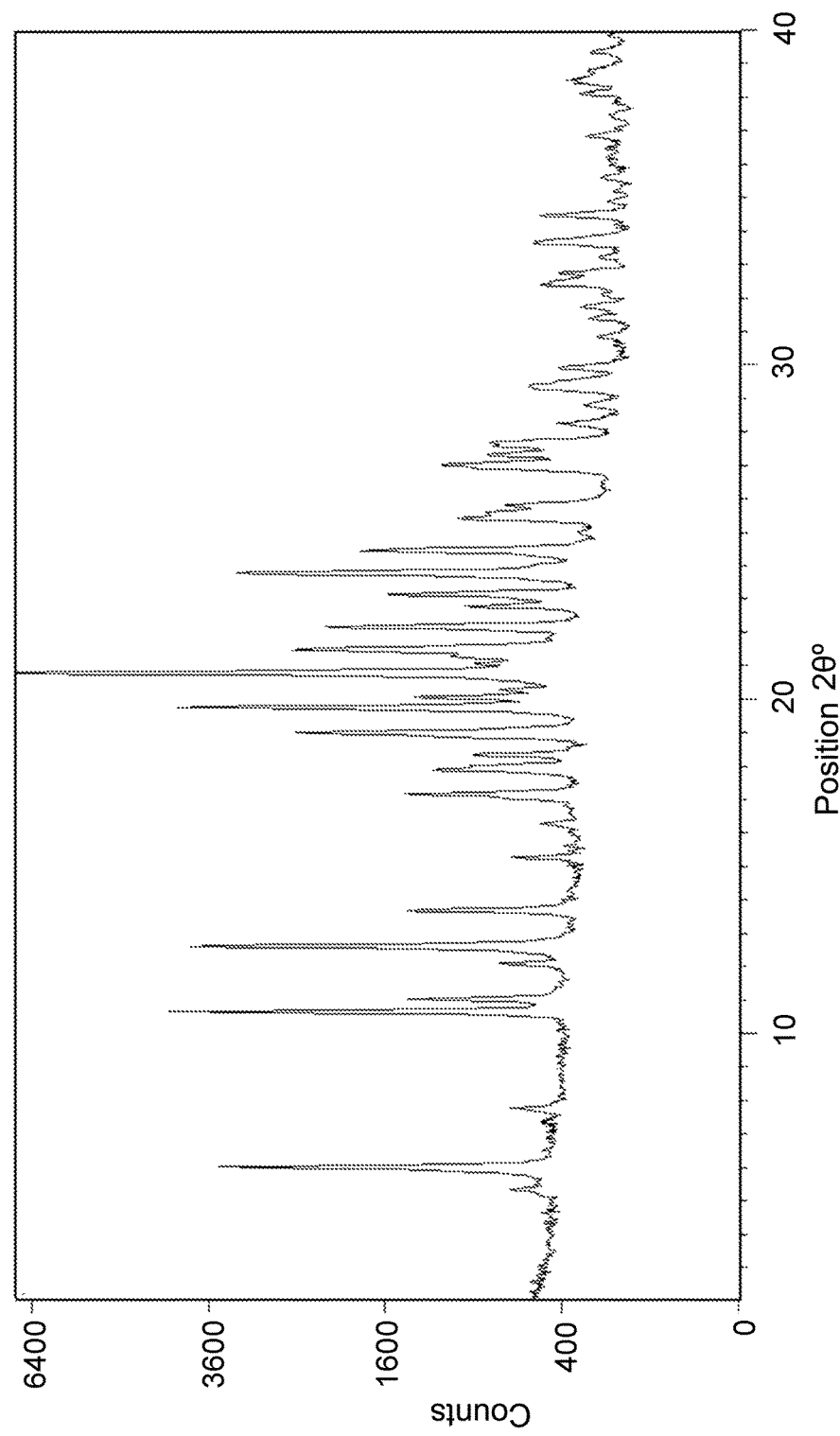
FIG. 2 shows the X-ray powder diffractogram of the gamma polymorph of silodosin obtained in Examples 3 and 4.

The maleic acid salt of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate of formula (I) obtained in Example 2 (1 kg) and dimethylsulfoxide (DMSO, 6 L) were loaded in a reactor, and the mixture was stirred. A 5 N sodium hydroxide solution (1.4 L) was then added. 33% hydrogen peroxide (1.8 L) was slowly added maintaining the temperature at about 40° C. and the mixture of the reactor was kept at 40° C. for 15-30 min under stirring. A 5% aqueous sodium sulfite solution (1.9 L) was then added to the content of the reactor under stirring. A saturated sodium chloride aqueous solution of (8 L) was loaded in the same reactor. Next, toluene (10 L) was added and the content of the reactor was heated at 70° C. for at least 15 min. Stirring was stopped, the phases were left to separate, and the aqueous phase was removed. The content of the reactor was cooled and stirred for at least 2 h at 25° C. The suspension was centrifuged and left to drain, washed with toluene (5 L), and left to drain again. The X-ray powder diffractogram of the gamma polymorph of silodosin is shown in FIG. 2.

Example 4. Synthesis of the Gamma Polymorph of Silodosin

Silodosin obtained in Example 3 (1 kg), water (5 L), and toluene (18 L) were loaded in a reactor and stirred at 65° C. The mixture was left to decant and the aqueous phase was removed. The mixture was stirred and heated at 65° C. until complete dissolution. The solution was cooled at 50° C. and seeded with gamma silodosin. The content of the reactor was cooled and the suspension was stirred at 25° C. for at least 2 h. The suspension was centrifuged, washed with toluene, and left to drain. The X-ray powder diffractogram of the gamma polymorph of silodosin is shown in FIG. 2. The gamma polymorph of silodosin obtained has a $D_{90}$ of 200 μm to 800 μm. The solid obtained was then milled and micronized, obtaining gamma polymorph of silodosin with the following particle sizes:

milled gamma polymorph of silodosin $D_{90}$=45.5 μm and D[4,3]=20.1 μm;

micronized gamma polymorph of silodosin $D_{90}$=12 μm and D[4,3]=6.8 μm.

Example 5. Synthesis of the Beta Polymorph of Silodosin

Figure 3:
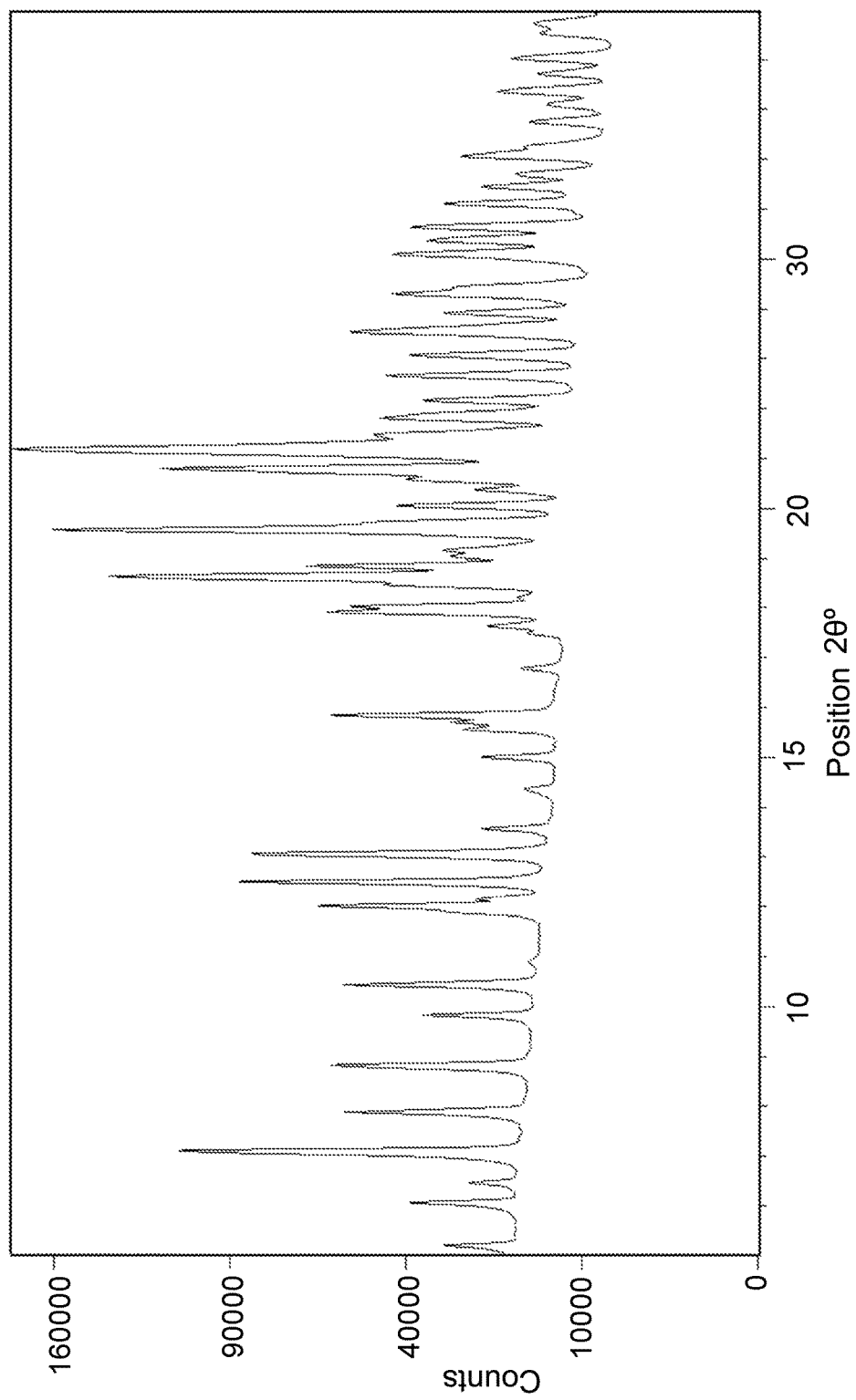
FIG. 3 shows the X-ray powder diffractogram of the beta polymorph of silodosin obtained in Example 5.

Silodosin obtained in Example 4 (1 kg) and isopropyl acetate (15 L) were loaded in a reactor. The mixture was stirred and heated at 70-75° C. until complete dissolution. It was cooled at 50° C. and seeded with beta silodosin. It was stirred at 50° C. for 30 min. It was gradually cooled to 0-5° C. and kept at this temperature for 1 h. The product was centrifuged and washed with isopropyl acetate (5 L). It was vacuum dried at 75° C. for 4 h. The X-ray powder diffractogram of the beta polymorph of silodosin obtained is shown in FIG. 3. The beta polymorph of silodosin obtained has a $D_{90}$ of 200 μm to 800 μm. The solid obtained was then milled, obtaining beta polymorph of silodosin with the following particle sizes: $D_{90}$=73.7 μm, $D_{50}$=27.5 μm, D[4,3]=37.7 μm.

Example 6. Silodosin Formulations

Ingredients of the formulations (the amounts are expressed as % p/p):
Silodosin (beta or gamma): 2.3%
Mannitol: 80.7%
Starch 1500, pregelatinized: 15.0%
Sodium lauryl sulfate: 1.0%
Magnesium stearate: 1.0%

The silodosin formulations were prepared by means of simply mixing the components, first mixing silodosin (using the particle sizes and polymorphs described in Examples 4 and 5) with mannitol, and then mixing other ingredients of the formulation. Finally, it was encapsulated and introduced into 90 g/m² PVC-PVDC (polyvinyl chloride-polyvinylidene chloride) blister packs. A part was introduced into HDPE (high-density polyethylene) flasks.

The invention claimed is:
1. Maleic acid salt of formula (I)

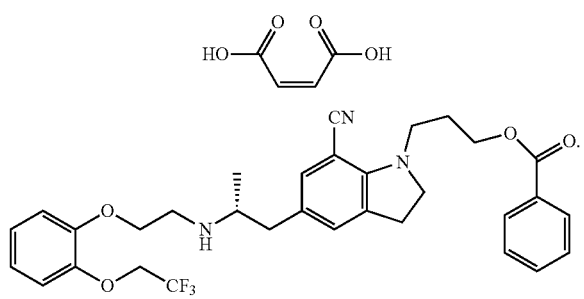

2. The salt of formula (I) according to claim 1 in crystalline form, characterized in that said salt has an X-ray powder diffractogram (recorded with a copper X-ray source) with peaks at 11.9, 14.6, 15.4, 17.1, 18.4, 21.0, 23.4, and 23.9 2θ°±0.2 2θ°.

3. The salt according to claim 2, characterized in that the X-ray powder diffractogram furthermore has peaks at 11.7, 14.4, 16.7, and 18.9 2θ°±0.2 2θ°.

4. A method for preparing the salt of formula (I) defined in claim 1, which comprises:
a) treating a compound of formula (II)

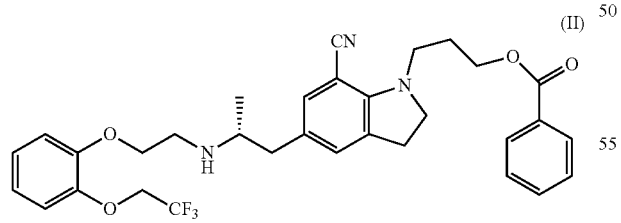

with maleic acid; and
b) isolating the salt of formula (I).

5. The method according to claim 4, wherein step a) is performed in a solvent selected from the group consisting of isopropanol, methanol, ethanol, n-propanol, tent-butanol, and n-butanol.

6. The method according to claim 4, further comprising treating a compound of formula (III) or a salt thereof

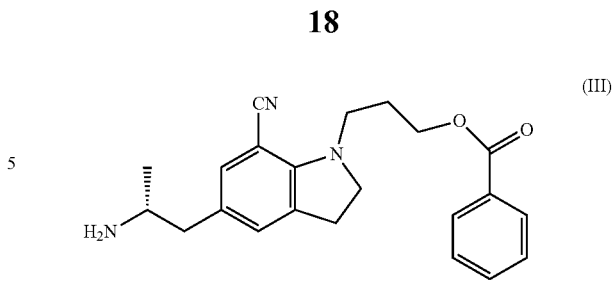

with a compound of formula (IV)

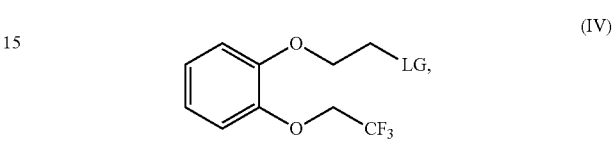

wherein LG is a leaving group,
in a polar aprotic solvent and in the presence of a base, to yield the compound of formula (II).

7. The method according to claim 6, wherein the tartaric acid salt of the compound of formula (III) is treated.

8. The method according to claim 7, wherein the tartaric acid salt is a (2R,3R)-(+)-tartaric acid salt.

9. The method according to claim 6, wherein the leaving group LG of the compound of formula (IV) is selected from the group consisting of methanesulfonyloxy, toluenesulfonyloxy, and trifluoromethanesulfonyloxy.

10. The method according to claim 6, wherein the polar aprotic solvent is acetonitrile.

11. The method according to claim 6, wherein the base is potassium carbonate.

12. A preparation method for preparing silodosin of formula (V)

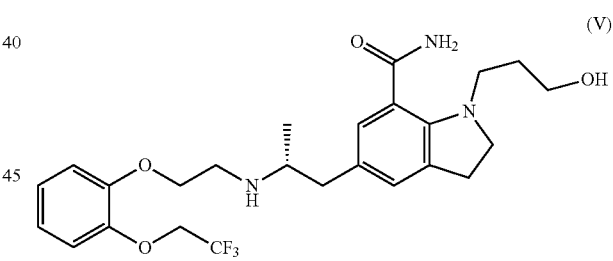

which comprises hydrolyzing a salt of formula (I)

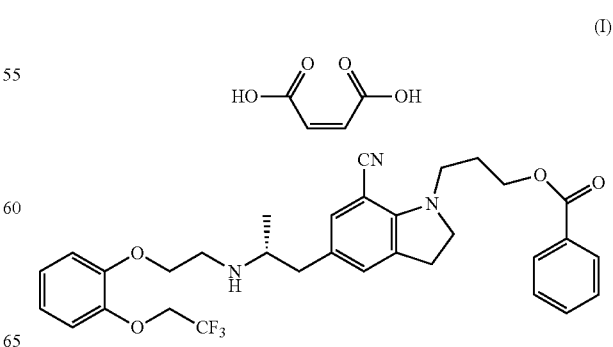

to yield silodosin of formula (V).

13. The method according to claim 12, further comprising
a) treating a compound of formula (II)

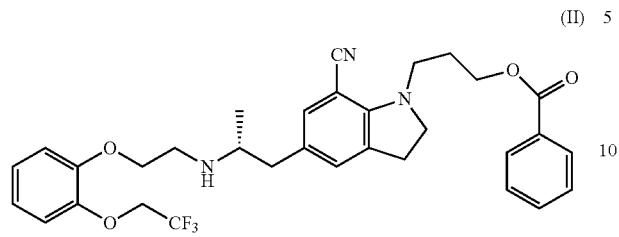
(II)

with maleic acid; and
b) isolating the salt of formula (I).

14. The method according to claim 12, wherein the hydrolysis is performed in the presence of an alkali metal hydroxide.

15. The method according to claim 14, wherein the alkali metal hydroxide is sodium hydroxide.

16. The method according to claim 12, wherein the hydrolysis is performed in the presence of an oxidizing agent.

17. The method according to claim 16, wherein the oxidizing agent is hydrogen peroxide.

18. The method according to claim 6, wherein the leaving group LG of the compound of formula (IV) is methanesulfonyloxy.

* * * * *

UNITED STATES PATENT AND TRADEMARK OFFICE
CERTIFICATE OF CORRECTION

PATENT NO. : 10,421,719 B2
APPLICATION NO. : 15/763689
DATED : September 24, 2019
INVENTOR(S) : José Luis Del Río Pericacho and Xavier Vila Tusell Page 1 of 1

It is certified that error appears in the above-identified patent and that said Letters Patent is hereby corrected as shown below:

In the Claims

Claim 5, Column 17, Line 64:
Delete "isopropanol, methanol, ethanol, n-propanol, tent-butanol,"
Insert --isopropanol, methanol, ethanol, n-propanol, tert-butanol,--

Signed and Sealed this
Third Day of December, 2019

Andrei Iancu
*Director of the United States Patent and Trademark Office*